United States Patent
Sezan et al.

(10) Patent No.: US 10,025,917 B2
(45) Date of Patent: Jul. 17, 2018

(54) BIOMETRICS FOR USER IDENTIFICATION IN MOBILE HEALTH SYSTEMS

(71) Applicant: QUALCOMM Incorporated, San Diego, CA (US)

(72) Inventors: Muhammed Ibrahim Sezan, Los Gatos, CA (US); John Keith Schneider, Williamsville, NY (US); Kenneth Kaskoun, La Jolla, CA (US); Eugene Dantsker, San Diego, CA (US)

(73) Assignee: QUALCOMM Incorporated, San Diego, CA (US)

(*) Notice: Subject to any disclaimer, the term of this patent is extended or adjusted under 35 U.S.C. 154(b) by 0 days.

(21) Appl. No.: 15/632,219

(22) Filed: Jun. 23, 2017

(65) Prior Publication Data

US 2017/0286661 A1    Oct. 5, 2017

Related U.S. Application Data

(62) Division of application No. 14/268,245, filed on May 2, 2014, now Pat. No. 9,721,409.

(51) Int. Cl.
*G06F 21/32* (2013.01)
*G06F 19/00* (2018.01)
(Continued)

(52) U.S. Cl.
CPC .............. *G06F 21/32* (2013.01); *A61B 5/01* (2013.01); *A61B 5/02438* (2013.01);
(Continued)

(58) Field of Classification Search
CPC ........... G06K 9/00906; G06K 9/00912; G06K 9/00919; G06K 9/00926; G06K 9/6289;
(Continued)

(56) References Cited

U.S. PATENT DOCUMENTS 6,929,636 B1   8/2005   Von
6,949,081 B1   9/2005   Chance
(Continued)

FOREIGN PATENT DOCUMENTS

EP       2600319 A1    6/2013
WO    2014009876       1/2014

OTHER PUBLICATIONS

US 8,613,701, 12/2013, Rao et al. (withdrawn)
(Continued)

*Primary Examiner* — Brian Miller
(74) *Attorney, Agent, or Firm* — Weaver Austin Villeneuve & Sampson LLP

(57) ABSTRACT

A wearable device may include a sensor system capable of obtaining physiological from a user's body. Some wearable devices may include a substance delivery system. A sensor system of a wearable device may include at least one "bio-assurance sensor" capable of obtaining biometric data that may be used to identify a user. For example, the bio-assurance sensor may be used to ensure that the wearable device is not removed from the user's body and/or placed on or in another user's body. In some examples, the wearable device may be used with a second device, such as a smart phone, that includes at least one "authentication sensor," such as a fingerprint sensor, that also may be used to identify a user. However, in some implementations the wearable device may include at least one authentication sensor.

20 Claims, 8 Drawing Sheets

(51) Int. Cl.
 *G06F 21/35* (2013.01)
 *A61B 5/01* (2006.01)
 *A61B 5/024* (2006.01)
 *A61B 5/145* (2006.01)
 *A61B 5/00* (2006.01)
 *A61B 5/11* (2006.01)
 *A61B 5/1172* (2016.01)
 *A61B 5/1171* (2016.01)
 *G16H 10/60* (2018.01)

(52) U.S. Cl.
 CPC .......... *A61B 5/1118* (2013.01); *A61B 5/1171* (2016.02); *A61B 5/1172* (2013.01); *A61B 5/14532* (2013.01); *A61B 5/4812* (2013.01); *A61B 5/6823* (2013.01); *A61B 5/6824* (2013.01); *G06F 19/3468* (2013.01); *G06F 21/35* (2013.01); *G06F 19/322* (2013.01); *G16H 10/60* (2018.01)

(58) Field of Classification Search
 CPC .......... G06K 9/00597; G06K 9/00604; G06K 9/0061; G06K 9/00617; G06T 2207/30196; G06T 2207/30216; H04N 1/624; A61B 5/113; A61B 5/115; G08B 21/04; G07C 9/00563; G07C 2009/00095; G07C 9/00158; G06F 21/32
 See application file for complete search history.

(56) References Cited

U.S. PATENT DOCUMENTS

| | | | |
|---|---|---|---|
| 6,957,771 | B2 | 10/2005 | Norris et al. |
| 7,039,812 | B2 | 5/2006 | Kawan et al. |
| 7,221,928 | B2 | 5/2007 | Laird et al. |
| 7,404,086 | B2 | 7/2008 | Sands et al. |
| 8,070,060 | B2 | 12/2011 | Schneider et al. |
| 8,070,742 | B2 | 12/2011 | Woo |
| 8,157,730 | B2 | 4/2012 | LeBoeuf et al. |
| 8,183,998 | B2 | 5/2012 | Rao et al. |
| 8,284,046 | B2 | 10/2012 | Allen et al. |
| 8,736,441 | B2 | 5/2014 | Rao et al. |
| 8,934,839 | B2 | 1/2015 | Singh |
| 8,976,007 | B2 | 3/2015 | Dugan et al. |
| 9,020,208 | B2 | 4/2015 | Whillock et al. |
| 9,112,701 | B2 | 8/2015 | Sano et al. |
| 9,125,979 | B2 | 9/2015 | Behzadi et al. |
| 9,558,336 | B2 * | 1/2017 | Lee .............. A61B 5/681 |
| 9,721,409 | B2 * | 8/2017 | Sezan ............ A61B 5/1171 |
| 2003/0154382 | A1 | 8/2003 | Vicard |
| 2005/0071647 | A1 | 3/2005 | Fujinuma et al. |
| 2005/0116811 | A1 | 6/2005 | Eros et al. |
| 2005/0270140 | A1 | 12/2005 | Oh |
| 2006/0224046 | A1 * | 10/2006 | Ramadas .......... A61B 5/0002 600/300 |
| 2008/0015523 | A1 | 1/2008 | Baker |
| 2008/0045806 | A1 | 2/2008 | Keppler |
| 2009/0009284 | A1 | 1/2009 | Sako |
| 2009/0270743 | A1 | 10/2009 | Dugan et al. |
| 2009/0306498 | A1 | 12/2009 | Bodduluri et al. |
| 2009/0326595 | A1 | 12/2009 | Brockway et al. |
| 2011/0130635 | A1 | 6/2011 | Ross |
| 2012/0068820 | A1 | 3/2012 | Mollicone et al. |
| 2012/0229270 | A1 | 9/2012 | Morley et al. |
| 2013/0021154 | A1 | 1/2013 | Solomon et al. |
| 2013/0261794 | A1 | 10/2013 | Fauci |
| 2014/0159862 | A1 | 6/2014 | Yang et al. |
| 2014/0188770 | A1 | 7/2014 | Agrafiot et al. |
| 2015/0070134 | A1 | 3/2015 | Nagisetty et al. |
| 2015/0088546 | A1 | 3/2015 | Balram et al. |
| 2015/0317855 | A1 | 11/2015 | Sezan et al. |
| 2015/0379255 | A1 | 12/2015 | Konanur et al. |
| 2015/0381609 | A1 | 12/2015 | Dadu et al. |

OTHER PUBLICATIONS

International Preliminary Report on Patentability PCT/US2015/027304—ISA/EPO—dated Jul. 19, 2016.
International Search Report and Written Opinion—PCT/US2015/027304—ISA/EPO—dated Aug. 11, 2015.
Second Written Opinion of the IPEA—PCT-US2015/027304—ISA/EPO—dated Apr. 26, 2016.
Shin M., "Secure Remote Health Monitoring with Unreliable Mobile Devices," Journal of Biomedicine and Biotechnology, Hindawi Publishing Corporation, 2012, Article ID 546021, 5 pages.
"The Nymi White Paper", BIONYM, Nov. 19, 2013 (Nov. 19, 2013), XP055115588, p. 5-p. 6.

* cited by examiner

BIOMETRICS FOR USER IDENTIFICATION IN MOBILE HEALTH SYSTEMS

PRIORITY CLAIM

This application claims priority to, and is a divisional of, U.S. patent application Ser. No. 14/268,245, filed on May 2, 2014 and entitled "BIOMETRICS FOR USER IDENTIFICATION IN MOBILE HEALTH SYSTEMS," which is hereby incorporated by reference.

TECHNICAL FIELD

This disclosure relates generally to mobile health devices, methods and systems.

DESCRIPTION OF THE RELATED TECHNOLOGY

As mobile devices become more versatile, user authentication becomes increasingly important. Increasing amounts of personal information may be stored on and/or accessible by a mobile device. For example, some mobile devices may be capable of monitoring a user's physiological data. Systems including such devices can allow remote monitoring of a user's physiological data. Although such systems have great potential value in the health care industry, they pose challenges, e.g., with regard to the privacy of patients' personal information.

SUMMARY

The systems, methods and devices of the disclosure each have several innovative aspects, no single one of which is solely responsible for the desirable attributes disclosed herein.

One innovative aspect of the subject matter described in this disclosure can be implemented in a device that may include a sensor system, a wireless interface system and a control system. The sensor system may include one or more biometric sensors. The sensor system may be capable of obtaining first biometric data from a user's body. In some examples, the first biometric data may include fingerprint data, voice data, retinal data, data indicating electrical activity of the user's heart, hair follicle data, pore data, skin papilla data and/or sub-dermal blood vessel data.

The control system may be capable of receiving the first biometric data from the sensor system and determining first biometric authentication information based on the first biometric data. The first biometric authentication information may include a representation of the first biometric data.

The control system may be capable of providing, via the wireless interface system, the first biometric authentication information to a second device. The control system may be capable of receiving, via the wireless interface system, a control signal from the second device and controlling the sensor system according to the control signal.

In some implementations, the control system may include secure processing and/or memory resources. For example, the control system may be capable of encrypting the first biometric authentication information. The control system may be capable of decrypting information, including but not limited to the control signal received from the second device.

According to some implementations, the sensor system may include one or more physiological sensors. The sensor system may be capable of obtaining physiological data from the user's body. The physiological data may include temperature data, respiration rate data, oxygen saturation data, blood glucose data, blood pressure data, heart rate data, data indicating electrical activity of the user's heart, actigraphy data and/or blood alcohol data.

In some implementations, the device may include a substance delivery system. The control system may be capable of controlling the substance delivery system according to the control signal.

According to some implementations, the control system may be capable of controlling the sensor system to obtain second biometric data from the user's body, of receiving the second biometric data from the sensor system and of determining second biometric authentication information based on the second biometric data. The control system may be capable of providing, via the wireless interface system, the second biometric authentication information to the second device.

In some examples, the second biometric data and the first biometric data may include different types of biometric data. The control system may be capable of determining whether the current user is an authorized user by comparing at least one of the first biometric information or the second biometric information with stored biometric information. The control system may be capable of associating the stored biometric information with at least one of the first biometric information or the second biometric information if the control system determines that the current user is the authorized user.

However, in some instances the second biometric data and the first biometric data may include one type of biometric data obtained at different times. The control system may, for example, be capable of controlling the sensor system to obtain the second biometric data periodically and/or upon the occurrence of an event. The control system may be capable of receiving, via the wireless interface system, an authentication indication from the second device indicating whether the user has been authenticated. The control system may be capable of controlling the device according to the authentication indication. In some implementations, the control system may be capable of preventing or ceasing at least one function of the device if the authentication indication indicates that the user has not been authenticated.

In some implementations, the device may be a wearable device. The device may include apparatus for securing the device to the user's body. For example, the apparatus for securing the wearable device to the user's body may include an arm band, a wrist band, an adhesive material, and/or a chest strap. In some instances, the wearable device may be capable of being implanted in the user's body.

Other innovative aspects of the subject matter described in this disclosure can be implemented in a wearable device that includes apparatus for securing the wearable device to a user's body. The wearable device may include a sensor system. The sensor system may include one or more biometric sensors. The sensor system may be capable of obtaining first biometric data and second biometric data from the user's body. The first biometric data may be a first type of biometric data and the second biometric data may be a second type of biometric data.

The wearable device may include a control system capable of receiving the first biometric data and the second biometric data from the sensor system. The control system may be capable of performing an authentication process based, at least in part, on the first biometric data and the second biometric data. In some implementations, the authentication process may be performed without reference to authentication information from an external device.

The control system may be capable of controlling the wearable device according to a result of the authentication process. In some examples, controlling the wearable device according to the result of the authentication process may involve preventing or ceasing at least one function of the wearable device if the authentication process indicates that the user has not been authenticated.

In some implementations, the wearable device may include an interface system. The sensor system may include one or more physiological sensors and may be capable of obtaining physiological data from the user's body. The control system may be capable of receiving physiological data from the sensor system and providing, via the wireless interface system, at least some of the physiological data to a second device. The physiological data may, for example, include temperature data, respiration rate data, oxygen saturation data, blood glucose data, blood pressure data, heart rate data, data indicating electrical activity of the user's heart, actigraphy data and/or blood alcohol data.

According to some implementations, the wearable device may include a substance delivery system. The control system may be capable of controlling the substance delivery system according to the authentication process.

Other innovative aspects of the subject matter described in this disclosure can be implemented in a mobile device that includes a biometric sensor system, a wireless interface system and a control system. The control system may be capable of receiving first biometric authentication information via the wireless interface system. The first biometric authentication information may correspond to first biometric data obtained from a user who is currently using a wearable device. The control system may be capable of obtaining second biometric data via the biometric sensor system and of determining second biometric information from the second biometric data.

The control system may be capable of determining whether the current user is an authorized user by comparing the second biometric information with stored biometric information. In some examples, the control system may be capable of associating the stored biometric information with the first biometric information if the control system determines that the current user is the authorized user. In some examples, the control system may be capable of disregarding signals from the wearable device if the control system determines that the current user is not the authorized user.

According to some implementations, the control system may be capable of sending, via the wireless interface system, a signal to the wearable device. The signal may, for example, include a signal indicating that the current user is the authorized user, a control signal instructing the wearable device to obtain physiological data from the current user and to provide at least some of the physiological data to the mobile device, a control signal instructing the wearable device to administer a substance to the current user and/or a control signal instructing the wearable device to provide a verification signal to the mobile device that a substance has been administered.

In some implementations, the control system may be capable of receiving, via the wireless interface system, physiological data from the wearable device. The control system may be capable of providing, via the wireless interface system, at least some of the physiological data to a remote server.

In some examples, the first biometric data may include fingerprint data, voice data, retinal data, data indicating electrical activity of the user's heart, hair follicle data, pore data, skin papilla data and/or sub-dermal blood vessel data. The second biometric data may, for example, include fingerprint data, voice data, retinal data, hair follicle data, pore data, skin papilla data or sub-dermal blood vessel data.

Other innovative aspects of the subject matter described in this disclosure can be implemented in a method that involves obtaining, via a sensor system of a wearable device, first biometric data from a user who is currently using the wearable device. The method may involve determining first biometric authentication information based on the first biometric data. The method may involve providing, via an interface system, the first biometric authentication information to a second device. The method may involve receiving, via the interface system, a signal from the second device. The method may involve controlling the wearable device according to the signal.

In some implementations, controlling the wearable device may involve obtaining physiological data from the user's body and/or administering a substance to the user. Controlling the wearable device may involve preventing or ceasing at least one function of the wearable device if the signal indicates (directly or indirectly) that the user has not been authenticated.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, other innovative aspects of the subject matter described in this disclosure can be implemented in a non-transitory medium having software stored thereon.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale. Like reference numbers and designations in the various drawings indicate like elements.

DETAILED DESCRIPTION

The following description is directed to certain implementations for the purposes of describing the innovative aspects of this disclosure. However, a person having ordinary skill in the art will readily recognize that the teachings herein may be applied in a multitude of different ways. It is contemplated that the described implementations may be included in or associated with a variety of electronic devices such as, but not limited to: mobile telephones, multimedia Internet enabled cellular telephones, mobile television receivers, wireless devices, smartphones, Bluetooth® devices, personal data assistants (PDAs), wireless electronic mail receivers, hand-held or portable computers, netbooks, notebooks, smartbooks, tablets, global positioning system (GPS) receivers/navigators, cameras, camcorders, wrist watches, electronic reading devices (e.g., e-readers), mobile health devices, etc. The teachings herein also may be used in applications such as, but not limited to, electronic switching devices, radio frequency filters, sensors, including but not limited to biometric sensors, accelerometers, gyroscopes, motion-sensing devices, magnetometers, inertial components for consumer electronics, parts of consumer electronics products, varactors, liquid crystal devices, electrophoretic devices, etc. Thus, the teachings are not intended to be limited to the implementations depicted solely in the Figures, but instead have wide applicability as will be readily apparent to one having ordinary skill in the art.

Some aspects of the present disclosure may be implemented in a wearable device. As used herein, the meaning of the term "wearable device" will encompass devices that may be worn by a user (e.g., via an arm band, a wrist band, a chest strap, etc.), devices that may be attached to a user's skin (e.g., via adhesive material) and devices that may be implanted, at least temporarily, in a user's body. In some implementations, a wearable device may include a sensor system capable of obtaining physiological data from the user's body, such as temperature data, respiration rate data, oxygen saturation data, blood glucose data, blood pressure data, heart rate data, blood alcohol data, etc. Some wearable devices may include a substance delivery system, such as a drug and/or hormone delivery system.

In some implementations disclosed herein, the sensor system may include at least one "bio-assurance sensor" capable of obtaining biometric data that may be used to identify or authenticate a user. For example, the bio-assurance sensor may be used to ensure that the wearable device is not removed from an authorized user's body and/or placed on or in another user's body who is not the authorized rightful user.

Figure 1A:
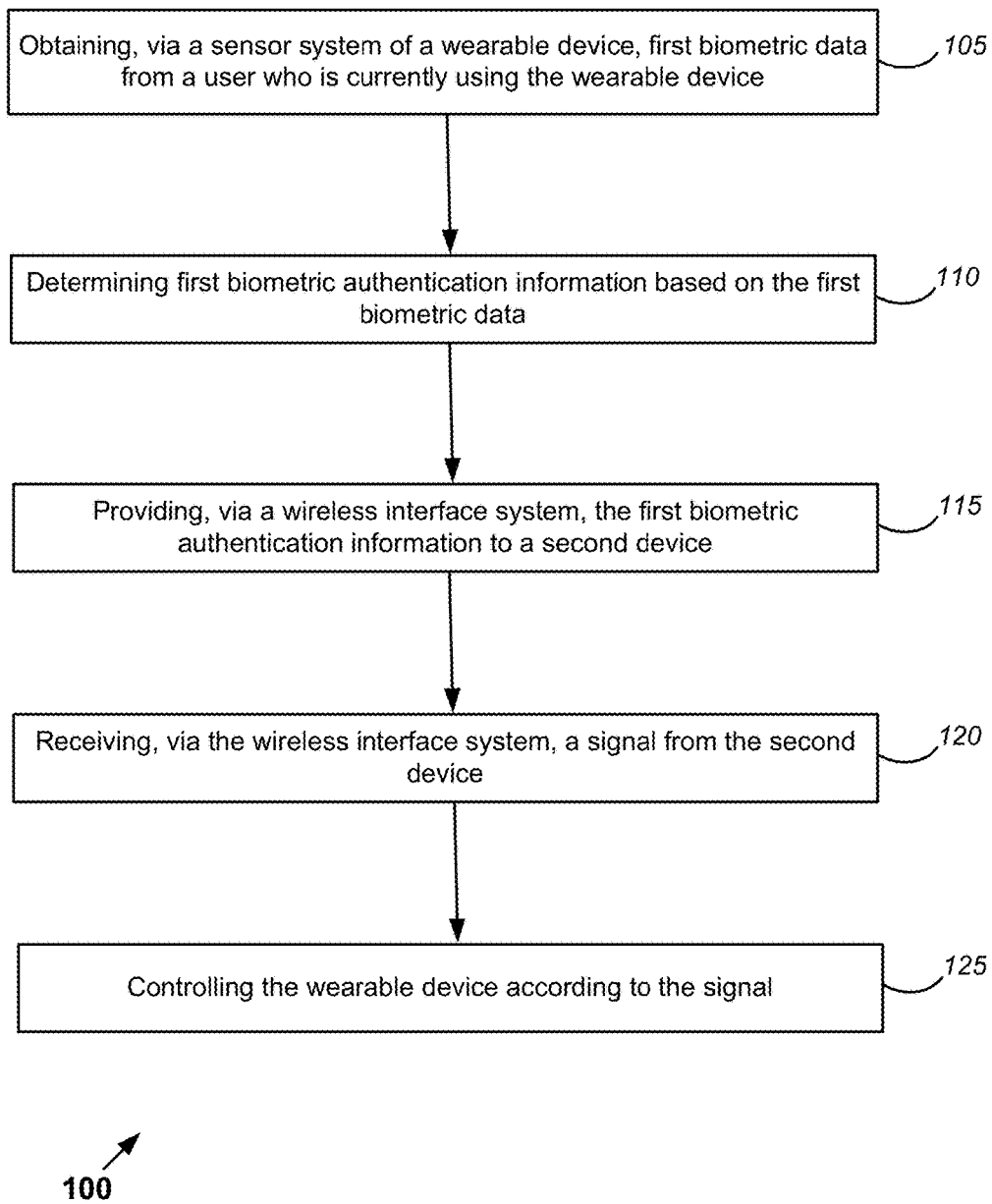
FIG. 1A is a flow diagram that outlines one example of a method for controlling a wearable device.

FIG. 1A is a flow diagram that outlines one example of a method for controlling a wearable device. The blocks of method 100, like other methods described herein, are not necessarily performed in the order indicated. Moreover, such methods may include more or fewer blocks than shown and/or described. In this example, block 105 involves obtaining, via a sensor system of a wearable device, first biometric data from a user who is currently using the wearable device. The first biometric data may be obtained by a "bio-assurance sensor." In this implementation, block 110 involves determining first biometric authentication information based on the first biometric data. In some examples, block 105 may involve obtaining image data and block 110 may involve extracting features from the image data.

In this example, block 115 involves providing, via an interface system, the first biometric authentication information to a second device. In some implementations, the interface system may include a wireless interface system. In some examples, the second device may be a mobile device, such as a smart phone, a smart watch, a tablet device, etc. However, in alternative implementations the second device may be a laptop computer or another type of device. In some examples, the second device may be capable of performing an authentication process based, at least in part, on the first biometric authentication information. In some implementations, the second device may include at least one "authentication sensor," such as a fingerprint sensor or other biometric sensor. The second device may be capable of determining second biometric information based on second biometric data obtained via the authentication sensor. In some examples, the second device may be capable of performing an authentication process based on the first biometric authentication information and/or the second biometric information. Alternatively, or additionally, in some implementations the wearable device may include at least one authentication sensor. In some such implementations, the wearable device may be capable of authentication functionality. Various examples of the foregoing implementations are described below.

Here, block 120 involves receiving, via the interface system, a signal from the second device. In this implementation, block 125 involves controlling the wearable device according to the signal. For example, controlling the wearable device may involve preventing or ceasing at least one function of the wearable device if the signal indicates (directly or indirectly) that the user has not been authenticated. The signal may, for example, indicate that the wearable device should prevent or cease at least one function without expressly indicating that the user has not been authenticated. If the second device has authenticated the user, the signal may indicate that the wearable device should perform at least one function. For example, block 125 may involve obtaining physiological data from the user's body and/or administering a substance, such as a drug or a hormone, to the user.

Figure 1B:
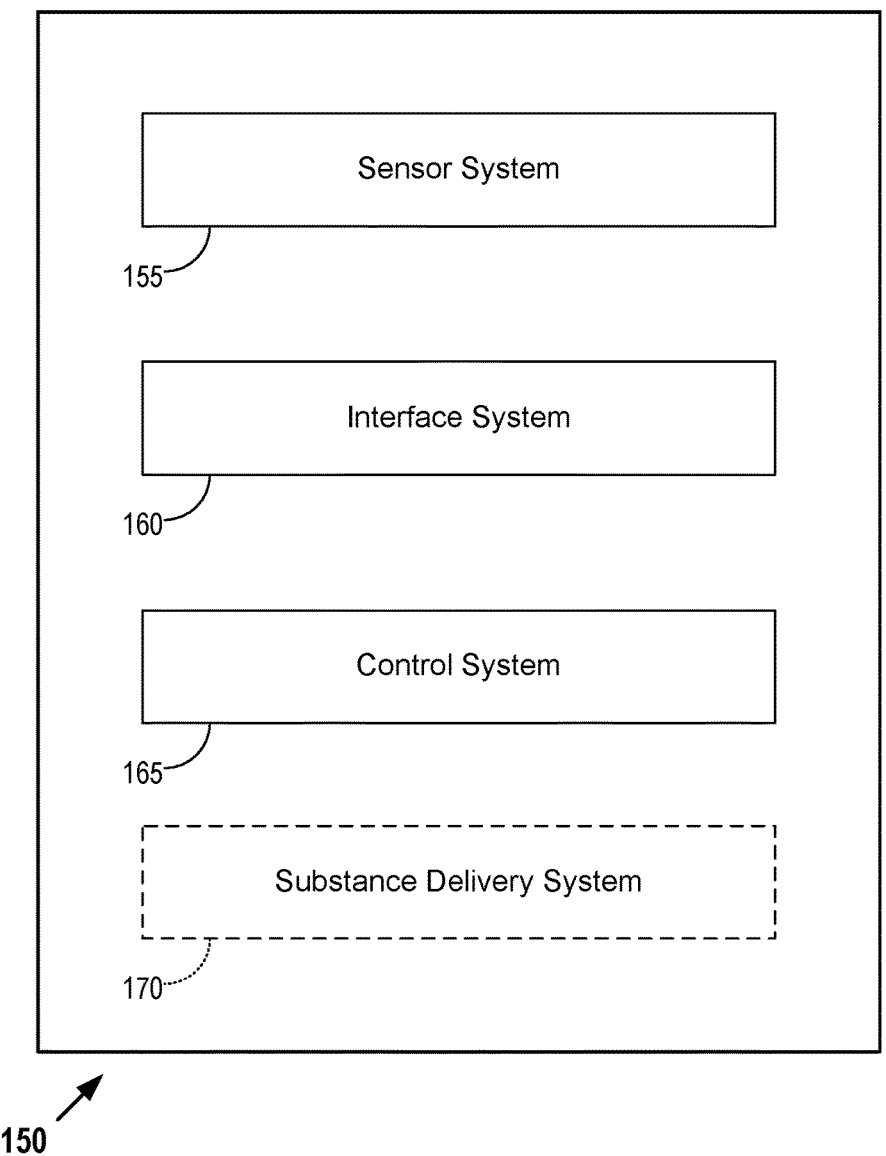
FIG. 1B is a block diagram that shows examples of components of a device in which some aspects of the present disclosure may be implemented.

FIG. 1B is a block diagram that shows examples of components of a device in which some aspects of the present disclosure may be implemented. In this example, the device is a wearable device. In the implementation shown in FIG. 1B, the wearable device 150 includes a sensor system 155, an interface system 160 and a control system 165. The interface system 160 includes a wireless interface system in this example. In some implementations, the interface system 160 may include a network interface, an interface between the control system 165 and a memory system and/or an external device interface (e.g., a port). In some implementations, the wearable device 150 may include a substance delivery system 170, which may include a drug delivery system and/or a hormone delivery system. In some examples, as noted elsewhere herein, controlling the wearable device may involve administering a substance to the user via the substance delivery system 170.

As noted above, the term "wearable device" encompasses devices that may be worn by a user (e.g., via an arm band, a wrist band, a chest strap, etc.), devices that may be attached to a user's skin (e.g., via adhesive material) and devices that may be implanted, at least temporarily, in a user's body. Accordingly, the wearable device 150 may include apparatus for securing the device to the user's body and/or for implanting the device in the user's body.

Figure 2:
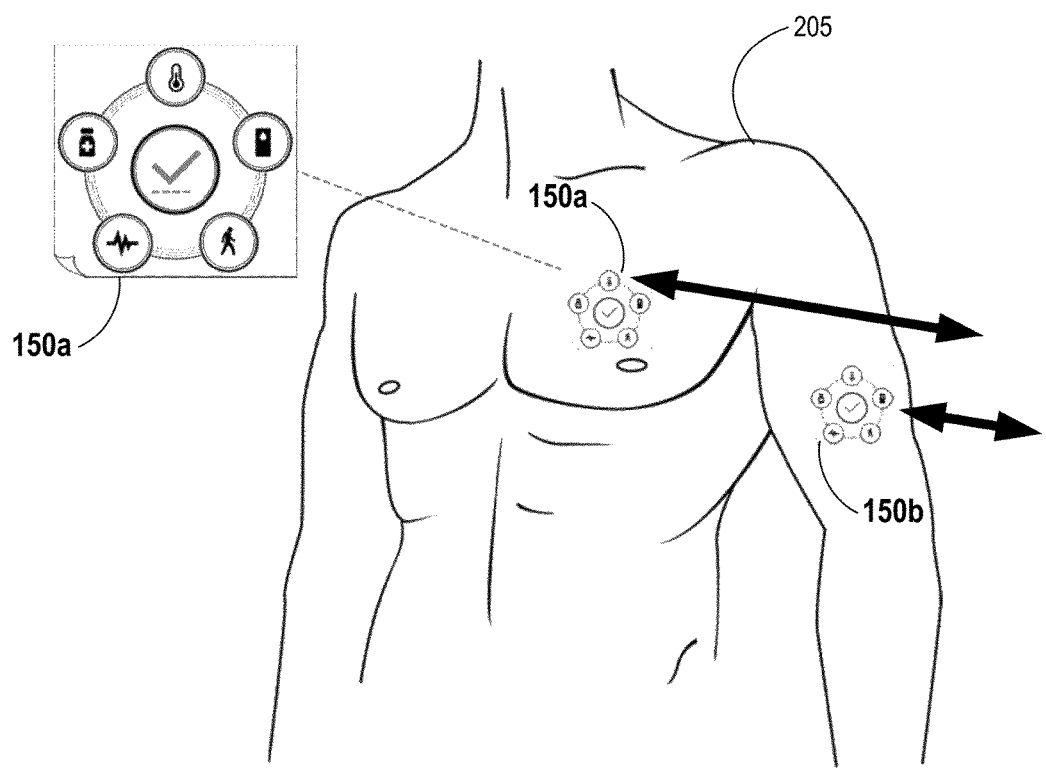
FIG. 2 shows an example of wearable devices on a user's body.

FIG. 2 shows an example of wearable devices on a user's body. In this example, the wearable device 150*a* is attached to a first area of the user's body 205 and the wearable device 150*b* is attached to a second area of the user's body 205. Here, the wearable device 150*a* is positioned near the user's heart. The wearable device 150*a* may include a sensor system 155 that is capable of monitoring heart rate data, data indicating electrical activity of the user's heart, the user's body temperature, etc. In the example shown in FIG. 2, the wearable device 150*b* is attached to one of the user's arms. In some implementations, the wearable device 150*b* may include a sensor system 155 that is capable of monitoring the user's body temperature, actigraphy data, the user's blood glucose data, blood alcohol data, etc. In some implementations, the wearable device 150*b* may include a substance delivery system, such as a drug and/or hormone delivery system.

FIG. 2 shows an enlarged view of the wearable device 150*a*. In this example, the wearable devices 150*a* and 150*b* include a thin layer that is capable of being attached to the user's body 205 via an adhesive. However, in alternative implementations, the wearable devices 150*a* and 150*b* may be configured for being worn by, attached to or implanted in a user's body via other apparatus, such as an arm band, a wrist band, a chest strap, etc. In this example, the dashes under the central check mark indicate a battery's remaining charge. As indicated by the two-headed arrows in FIG. 2, the wearable devices 150*a* and 150*b* are capable of communicating with one or more other devices via wireless interfaces on wireless networks.

Returning to FIG. 1B, in this example the sensor system 155 includes one or more biometric sensors, which may be considered as one or more examples of the "bio-assurance sensor" referenced elsewhere herein. In this example, the sensor system 155 is capable of obtaining first biometric data from a user's body.

In some implementations, for example, the first biometric data may include fingerprint data, voice data, retinal data, data indicating electrical activity of the user's heart, hair follicle data, pore data, skin papilla data and/or sub-dermal blood vessel data. For example, sensor system 155 may include an ultrasonic sensor capable of obtaining ultrasonic hair follicle image data, pore image data, skin papilla image data and/or sub-dermal blood vessel image data corresponding to a portion of the user's body on which the wearable device is being worn.

The control system 165 may include at least one of a general purpose single- or multi-chip processor, a digital signal processor (DSP), an application specific integrated circuit (ASIC), a field programmable gate array (FPGA) or other programmable logic device, discrete gate or transistor logic, or discrete hardware components. In this example, the control system 165 is capable of receiving the first biometric data from the sensor system 155 and of determining first biometric authentication information based on the first biometric data. The first biometric authentication information may include a representation of the first biometric data. The first biometric authentication information may, for example, include information regarding features extracted from the first biometric data.

For example, if the sensor system 155 includes an ultrasonic sensor capable of obtaining ultrasonic image data corresponding to a portion of the user's body on which the wearable device 150 is being worn, the process of determining first biometric authentication information may involve extracting features from the ultrasonic image data corresponding to the arrangement of hair follicles, dermal or sub-dermal patterns, blood vessel patterns, etc., in that portion of the user's body. The process of determining first biometric authentication information may involve creating a template of extracted features. The template may include information regarding the types of extracted features, the shapes of extracted features, the sizes of extracted features, the locations of extracted features, the orientations of extracted features, etc. Accordingly, determining first biometric authentication information may involve processes that are similar to fingerprint feature extraction and template creation processes.

The control system 165 may be capable of providing, via the interface system, the first biometric authentication information to a second device. According to some implementations, the control system 165 may include secure processing and/or memory resources. For example, in some implementations the control system 165 may be capable of encrypting the first biometric authentication information. In some examples, the second device may be capable of performing an authentication process based, at least in part, on the first biometric authentication information. The control system 165 may be capable of receiving, via the wireless interface system, a control signal from the second device and capable of controlling the sensor system 155 (and/or another component of the wearable device 150) according to the control signal. In some implementations the control system 165 may be capable of decrypting information, including but not limited to the control signal, received from the second device.

For example, if the second device determines that the user has not been authenticated, the control signal may indicate that the wearable device 150 should prevent or cease at least one function. The control signal may, for example, indicate that the wearable device 150 should prevent or cease at least one function without expressly indicating that the user has not been authenticated. However, in some implementations the control signal may include authentication information from the second device indicating whether the user has been authenticated. The control system 165 may be capable of controlling the wearable device 150 according to the authentication information.

If the second device has authenticated the user, the control signal may indicate that the wearable device 150 should perform at least one function. The function may vary according to the capabilities of the wearable device 150.

In some examples, the wearable device 150 may include a substance delivery system. In response to receiving the control signal from the second device, the control system 165 may control the substance delivery system to provide a drug, a hormone (e.g., a peptide hormone such as insulin), or another substance to the user.

In some implementations, the sensor system 155 may include one or more physiological sensors. In some implementations, in response to receiving the control signal from the second device, the control system 165 may control the sensor system 155 to obtain one or more types of physiological data. As used herein, the meaning of the term "physiological sensors" encompasses sensors that may be referred to by a person of skill in the art (POSITA) as physiological sensors or biological sensors. Accordingly, "physiological data" obtained by the physiological sensors may include what a POSITA might consider to be physiological data or biological data. As such, the sensor system 155 may be capable of obtaining temperature data, respiration rate data, oxygen saturation data, blood glucose data, blood pressure data, heart rate data, data indicating electrical activity of the user's heart, actigraphy data, blood alcohol data and/or other types of physiological data.

In some examples, the control system 165 may be capable of controlling the sensor system 155 to obtain second biometric data from the user's body. The control system 165 may be capable of receiving the second biometric data from the sensor system 155, of determining second biometric authentication information based on the second biometric data and of providing, via the wireless interface system, the second biometric authentication information to the second device.

In some implementations, the first biometric data and the second biometric data may be different types of biometric data. According to some such implementations, the control system 165 may be capable of authenticating the user based, at least in part, on the first and/or the second biometric authentication information. For example, the control system 165 may be capable of determining whether the current user is an authorized user by comparing the first biometric information and/or the second biometric information with stored biometric information. The control system 165 may be capable of associating the stored biometric information with the first biometric information and/or the second biometric information if the control system determines that the current user is the authorized user.

Figure 3:
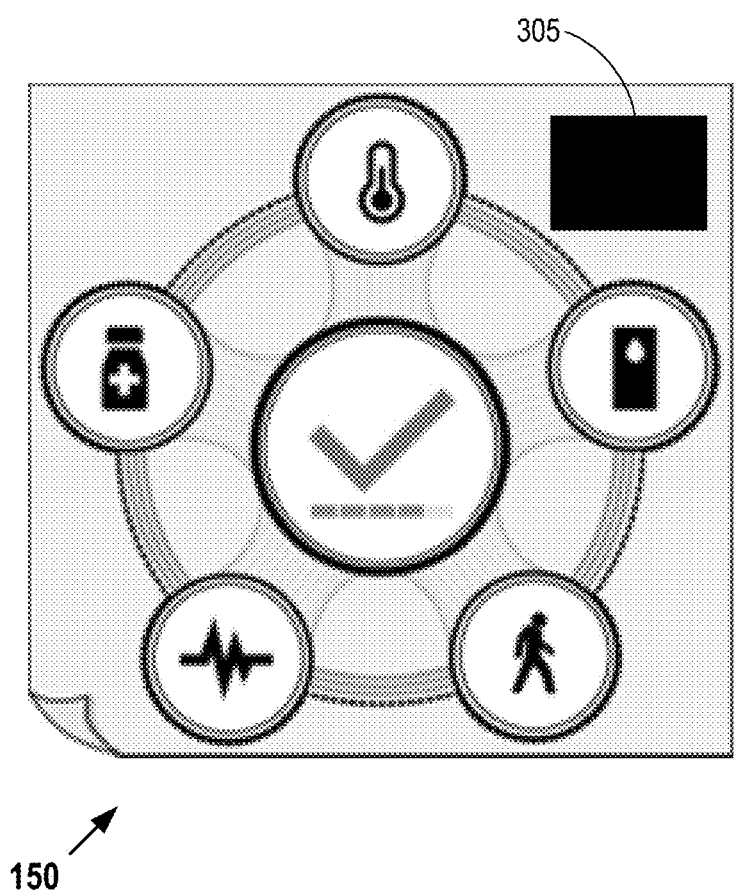
FIG. 3 shows an example of a wearable device that includes a fingerprint sensor.

For example, in some implementations the wearable device 150 may include a fingerprint sensor. FIG. 3 shows an example of a wearable device that includes a fingerprint sensor. Here, the wearable device 150c includes a fingerprint sensor 305. The fingerprint sensor 305 may be any convenient type of fingerprint sensor, such as an optical sensor, an ultrasonic sensor, a capacitive sensor, etc. Accordingly, the size, type and position of the fingerprint sensor 305 may vary according to the implementation. Like the wearable devices 150a and 150b shown in FIG. 2, the wearable device 150c includes adhesive material for attaching the wearable device 150c to a user's body. However, in alternative implementations, the wearable device 150c may be configured for being worn by, attached to or implanted in a user's body via other appropriate apparatus. Some implementations of the wearable device 150 may include a speaker, an actuator, a display or another device that the control system may be capable of controlling to prompt a user to provide biometric data, such as fingerprint data.

Accordingly, in some implementations the second biometric data may include a second type of biometric data, such as fingerprint data, obtained by a sensor of the wearable device 150. A control system (such as the control system 165 shown in FIG. 1B) may be capable of determining whether the current user is an authorized user by comparing the second biometric information (recently-obtained fingerprint information in this example) with stored biometric information (previously-obtained fingerprint information in this example).

In some implementations, the control system may be capable of controlling the sensor system 155 to obtain the second biometric data periodically or upon the occurrence of an event. For example, the control system 165 may be capable of controlling the sensor system 155 to obtain the second biometric data as input for an authentication process to be performed prior to delivery of a substance, via the wearable device 150, to a user.

In alternative examples, the first biometric data and the second biometric data may be the same type of biometric data obtained at different times. For example, the biometric data may include ultrasonic image data corresponding to a portion of the user's body on which the wearable device is being worn. The control system 165 may be capable of controlling the sensor system 155 to obtain ultrasonic image data periodically, or upon the occurrence of an event, without requiring any action on the part of the user. Accordingly, the process of obtaining additional instances of the same type of biometric data at different times may be performed without the user's knowledge. The control system 165 (or a control system of another device) may be capable of determining whether the current user is an authorized user by comparing the second biometric information (information based on recently-obtained ultrasonic image data in this example) with stored biometric information (information based on previously-obtained ultrasonic image data in this example). If, for example, the wearable device 150 has been moved to a different portion of the authorized user's body, or removed from the authorized user's body and placed on another user's body, the second biometric information should not match the stored biometric information and the authentication process should not terminate successfully. If the control system 165 (or a control system of another device) determines that the current user has not been authenticated, the control system may indicate that the wearable device 150 should prevent or cease at least one function.

At least some of the methods disclosed herein may be performed by one or more devices according to instructions (e.g., software) stored on non-transitory media. Such non-transitory media may include memory devices, including but not limited to random access memory (RAM) devices, read-only memory (ROM) devices, etc. In some implementations, the non-transitory media may be part of and/or accessible by a wearable device 150.

Figure 4:
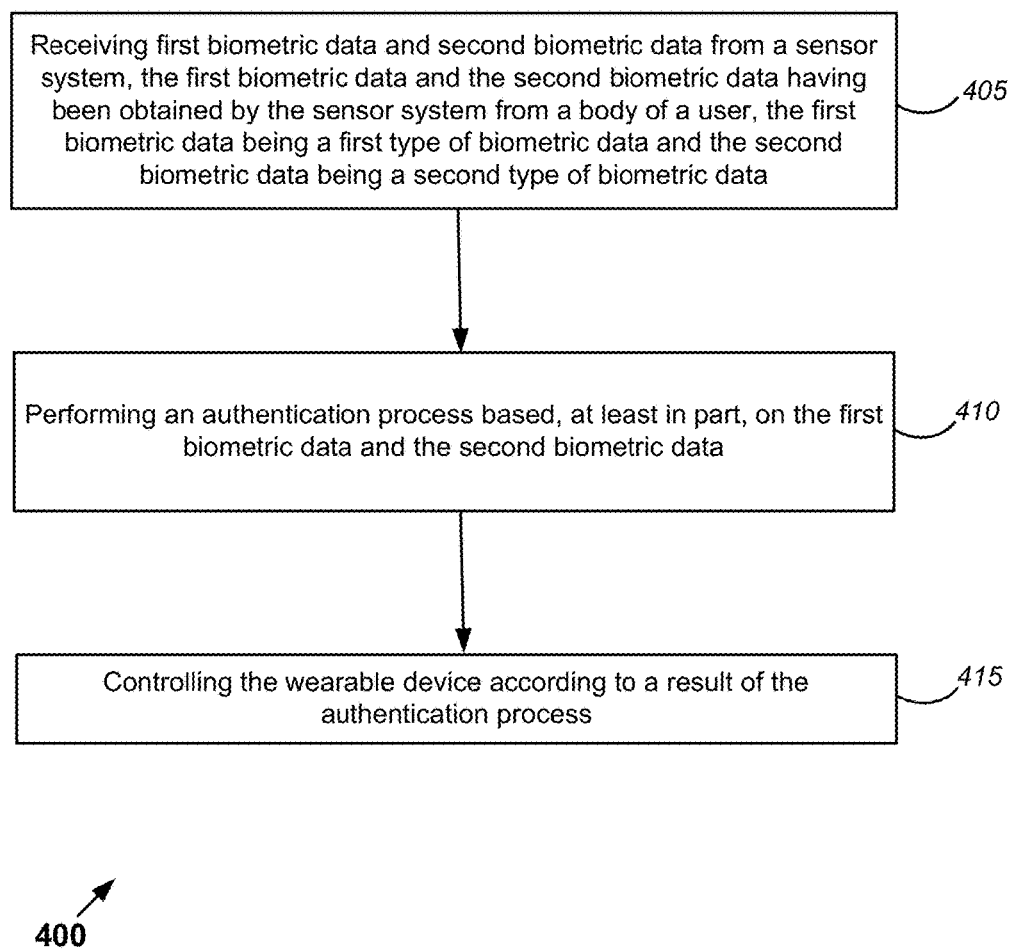
FIG. 4 is a flow diagram that outlines an example of a method for controlling a wearable device.

FIG. 4 is a flow diagram that outlines an example of a method for controlling a wearable device. According to some implementations, method 400 may be implemented in a non-transitory medium having software stored thereon. In this example, block 405 involves controlling a wearable device to receive first biometric data and second biometric data from a sensor system. The sensor system may be a sensor system of the wearable device. The first biometric data and the second biometric data may have been obtained by the sensor system from a body of a user currently using the wearable device.

In this example, the first biometric data is a first type of biometric data and the second biometric data is a second type of biometric data. However, in alternative implementations, the first biometric data and the second biometric data may be the same type of biometric data.

In this example, block 410 involves controlling the wearable device to perform an authentication process based, at least in part, on the first biometric data and the second biometric data. For example, the authentication process may involve determining first biometric information and second biometric information based on the first and second biometric data. The authentication process may involve comparing the first biometric information and second biometric information with stored biometric information that has been previously obtained from an authorized user. In the example shown in FIG. 4, the authentication process is performed by a control system of the wearable device and is based on biometric data obtained by the wearable device. Accordingly, the authentication process is performed without reference to authentication information from an external device. In this example, block 415 involves controlling the wearable device according to a result of the authentication process.

Figure 5:
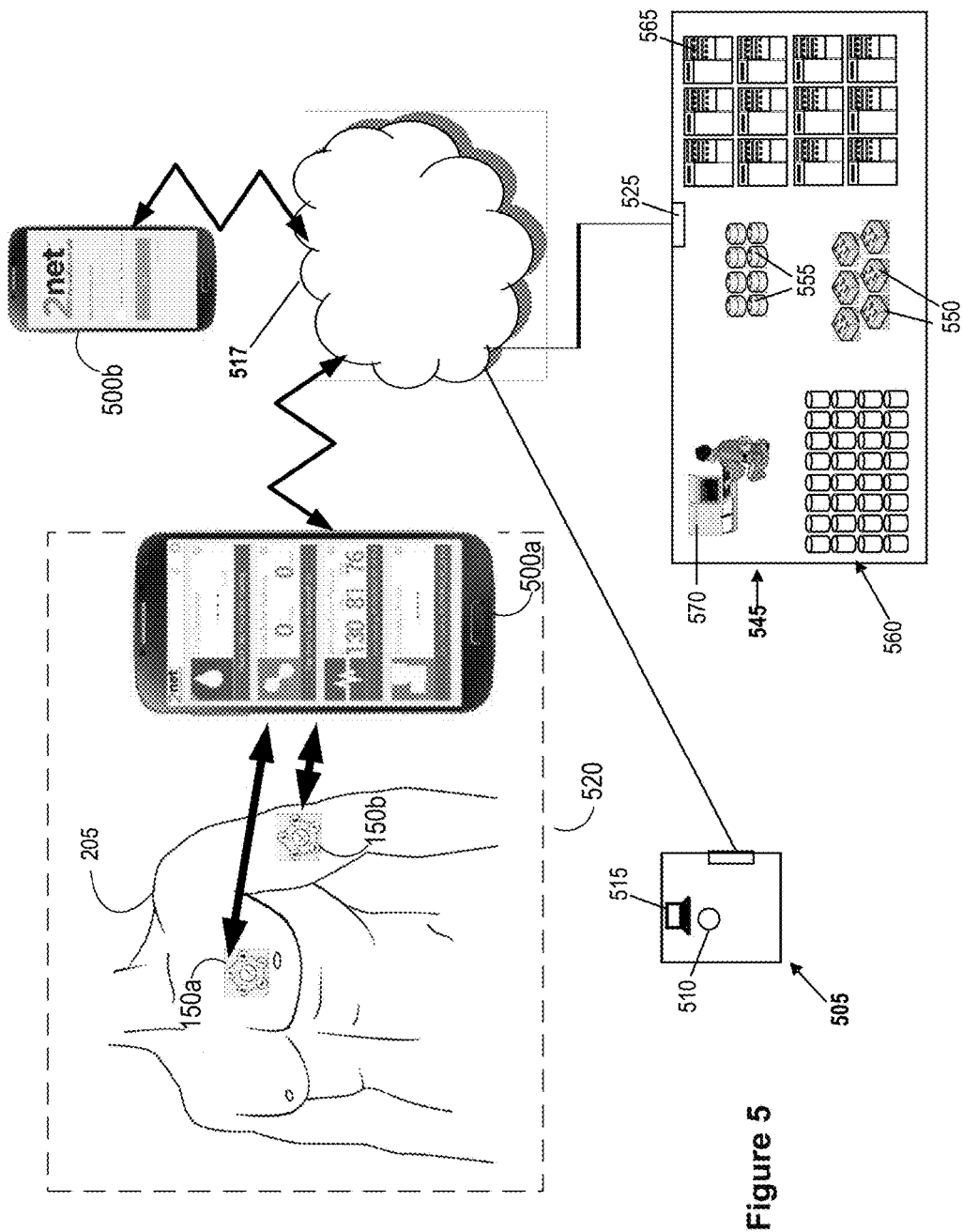
FIG. 5 is a block diagram that shows examples of components of a system in which some aspects of the present disclosure may be implemented.

FIG. 5 is a block diagram that shows examples of components of a system in which some aspects of the present disclosure may be implemented. The numbers, types and arrangements of devices shown in FIG. 5 are merely shown by way of example. In this example, various devices are capable of communication via one or more networks 517. The networks 117 may, for example, include the public switched telephone network (PSTN) and the Internet. The mobile devices 500a and 500b shown in FIG. 5 may, for example, be smart phones, cellular telephones, tablet devices, etc.

At location 520, a mobile device 500a is capable of wireless communication with the wearable devices 150a and 150b. The mobile device 500a is one example of a "second device" referenced in the foregoing discussion. The mobile device 500a may, for example, be capable of executing software to perform some of the methods described herein, such as authentication functionality, determining and sending control signals to the wearable devices 150a and 150b, receiving information from the wearable devices 150a and 150b, etc.

In this example, a data center 545 includes various devices that may be configured to provide health information services via the networks 517. Accordingly, the data center 545 is capable of communication with the networks 517 via the gateway 525. Switches 550 and routers 555 may be configured to provide network connectivity for devices of the data center 545, including storage devices 560, servers 565 and workstations 570. Although only one data center 545 is shown in FIG. 5, some implementations may include multiple data centers 545.

One or more types of devices in the data center 545 (or elsewhere) may be capable of executing middleware, e.g., for data management and/or device communication. Health-related information, including but not limited to information obtained by networked wearable devices 150 and/or other information regarding authorized users of wearable devices 150, may be stored on storage devices 560 and/or servers 565. Health-related software also may be stored on storage devices 560 and/or servers 565. In some implementations, some such health-related software may be available as "apps" and downloadable by authorized users.

In this example, various people and/or entities, including but not limited to health care professionals, patients, patients' families, insurance company representatives, etc., may obtain information regarding, or obtained by, networked wearable devices 150. The information may include, but is not limited to, physiological data obtained by one or more wearable devices 150, information regarding substance delivery by networked wearable devices 150, etc.

In some implementations, information regarding the type of substance delivered, the time of substance delivery, the dosage and/or other data may be transmitted by networked wearable devices 150 and stored in one or more devices of the data center 545. Additional information, such as time stamp information, authentication information and/or location information, may be associated with substance delivery information and/or physiological data obtained by one or more wearable devices 150. Such information may be used, for example, to create a record that substances were being administered to and/or data were being obtained from an authorized user/patient at specified times. Such information may be used to create an audit trail. In some implementations, such information may be used to enable mobile and/or remote clinical trials for drugs, instead of requiring participants in drug trials to have drugs administered only in a particular location, such as a medical research center.

In some examples, authorized people and/or entities may obtain such information via the data center 545. Alternatively, at least some people and/or entities may be authorized to obtain such information via a data feed from networked wearable devices 150. One or more other devices (such as mobile devices 500 or devices of the data center 545) may act as intermediaries for such data feeds. Such devices may, for example, be capable of applying data filtering algorithms, executing data summary and/or analysis software, etc. In some implementations, data filtering, summary and/or analysis software may be available as "apps" and downloadable (e.g., from the data center 545) by authorized users.

In this example, a family member of an authorized user is logging into the system, via the mobile device 500b, in order to access physiological data obtained by wearable devices 150a and 150b from the user's body 205. FIG. 5 also depicts a doctor's office 505, from which a health care professional 510 is using a laptop 515 to access information from the data center 545. The information may include information obtained by (and/or substances delivered by) wearable devices 150a and 150b, or by other networked wearable devices 150.

Figure 6:
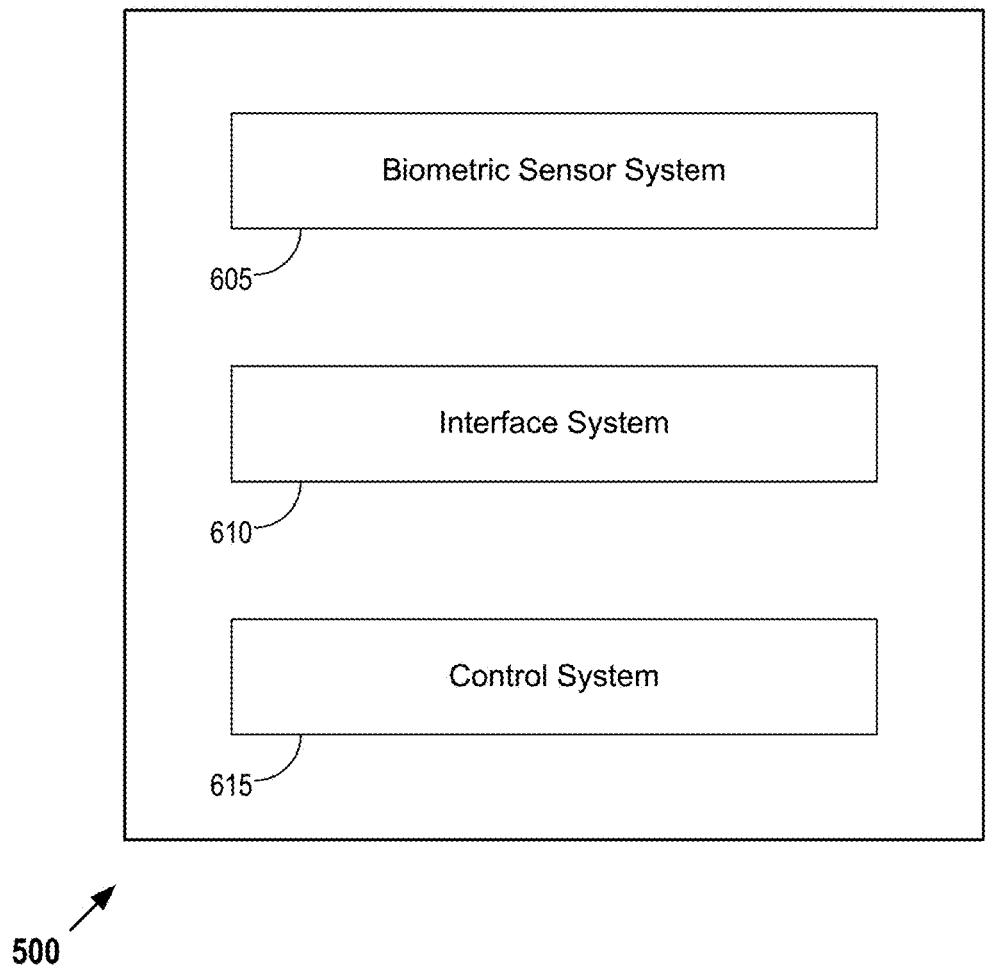
FIG. 6 is a block diagram that shows examples of components of a mobile device in which some aspects of the present disclosure may be implemented.

FIG. 6 is a block diagram that shows examples of components of a mobile device in which some aspects of the present disclosure may be implemented. In this example, the mobile device 500 includes a biometric sensor system 605, an interface system 610 and a control system 615. The biometric sensor system 605 may include one or more types of biometric sensor, such as a retinal scanner, a fingerprint sensor, etc. The interface system 610 includes a wireless interface system in this example. In some implementations, the interface system 610 may include a network interface, an interface between the control system 615 and a memory system and/or an external device interface (e.g., a port).

The control system 615 may include at least one of a general purpose single- or multi-chip processor, a digital signal processor (DSP), an application specific integrated circuit (ASIC), a field programmable gate array (FPGA) or other programmable logic device, discrete gate or transistor logic, or discrete hardware components.

Figure 7:
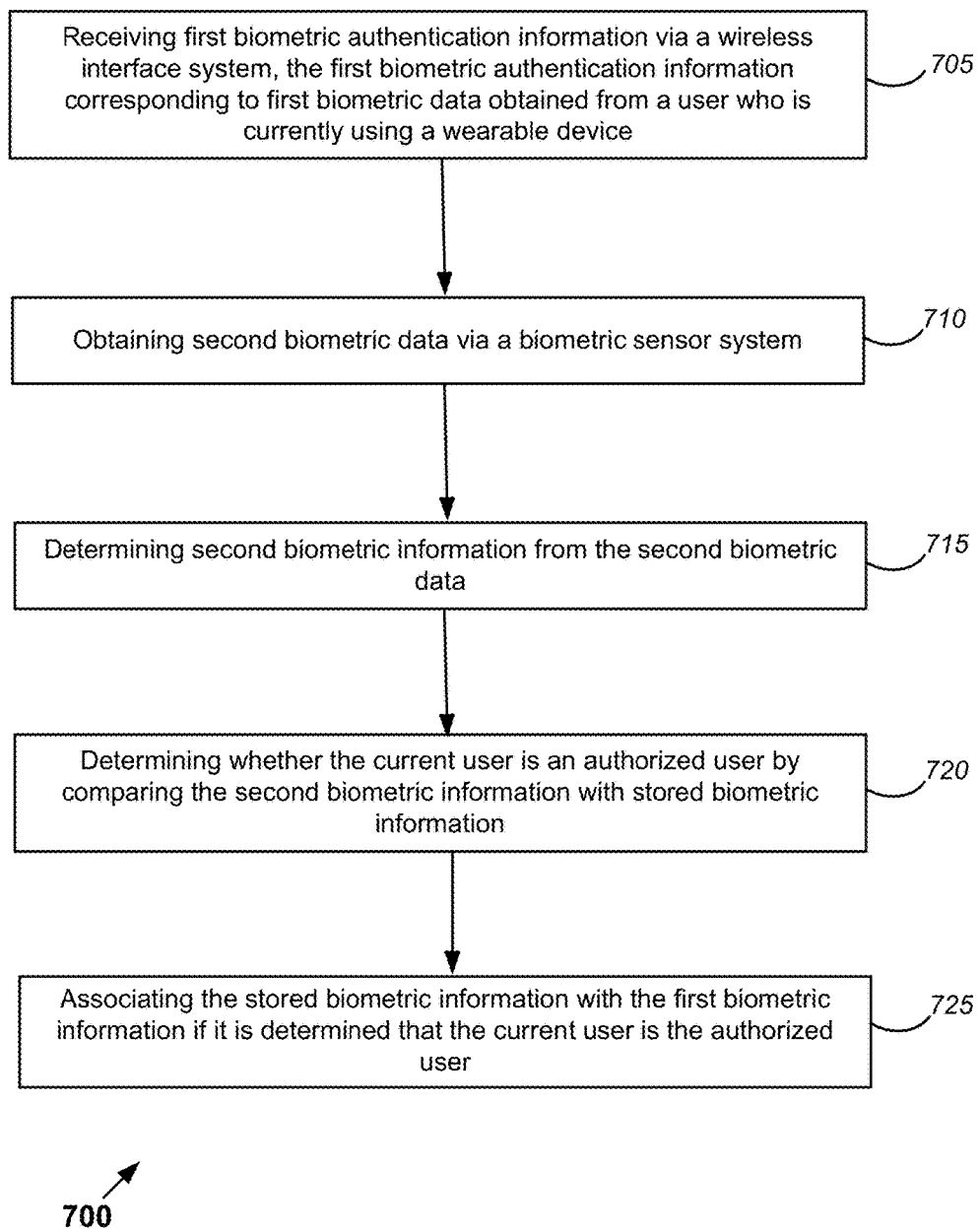
FIG. 7 is a flow diagram that outlines an example of a method for controlling a mobile device such as that shown in FIG. 6.

FIG. 7 is a flow diagram that outlines an example of a method for controlling a mobile device such as that shown in FIG. 6. According to some implementations, method 700 may be implemented in a non-transitory medium having software stored thereon. In some implementations, method 700 may be performed, at least in part, by a control system of a mobile device (e.g., by control system 615). Method 700 may, for example, be performed when a user first attaches a wearable device 150 to the user's body.

In this example, block 705 involves receiving first biometric authentication information via a wireless interface system. In this example, the first biometric authentication information corresponds to first biometric data obtained from a user who is currently using a wearable device.

In this implementation, block 710 involves obtaining second biometric data via a biometric sensor system. For example, the second biometric data may be obtained via the biometric sensor system 605 of FIG. 6. In some implementations, the second biometric data may include fingerprint data, e.g., fingerprint image data. The second biometric data may, for example, be obtained from a user seeking to obtain access to and/or control one or more wearable devices currently attached to the user's body.

In this example, block 715 involves determining second biometric information based on the second biometric data. The second biometric information may, for example, include a representation of the second biometric data. The second biometric information may, for example, include information regarding features extracted from the second biometric data.

Here, block 720 involves determining whether the current user of the wearable device is an authorized user by comparing the second biometric information with stored biometric information. For example, block 720 may involve comparing recently-obtained fingerprint template information with previously-obtained fingerprint template information of an authorized user. The stored biometric information may, for example, have been obtained from the authorized user during an enrollment procedure during which the authorized user was reliably identified.

In this implementation, block 725 involves associating the stored biometric information with the first biometric information if it is determined that the current user is the authorized user. For example, the mobile device may create a data structure, such as an encrypted data structure, that includes the stored biometric information and the first biometric information. Alternatively, or additionally, the mobile device may send a code (such as an encrypted and/or unique code) to a data center, to an authorized entity, etc., authenticating the user and indicating that biometric information acquired by a wearable device has been successfully associated with biometric information of an authorized user.

If it is determined in block 720 that the current user is not the authorized user, a control system of a mobile device (e.g., by control system 615) may take one or more of various actions. For example, the control system may prompt a user to provide the second biometric data again. For instance, a user may sometimes fail to present a digit in a manner that allows useable fingerprint data to be acquired. The user may be given a predetermined number of opportunities to provide the second biometric data. Alternatively, or additionally, the user may be given at least one opportunity to provide another type of biometric data.

As another example, the control system may send a corresponding message to another device, e.g., to a device of a data center. In some implementations, the control system may disregard further signals from the wearable device if the control system determines that the current user is not the authorized user. This capability may be advantageous, for example, for implementations involving wearable devices that only have transmission capability but not "receive capability" for receiving control signals from the mobile device. Some such wearable devices may, for example, include a sensor system having one or more physiological sensors, but no substance delivery system. Alternatively, such wearable devices may include a passive transdermal substance delivery system wherein substance delivery occurs via osmosis and is not controllable except by removing the wearable device.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

What is claimed is:

1. A wearable device, comprising:
   apparatus for securing the wearable device to a user's body;
   a sensor system including one or more biometric sensors, the sensor system being capable of obtaining first biometric data and second biometric data from the user's body, the first biometric data being a first type of biometric data and the second biometric data being a second type of biometric data;
   a substance delivery system; and
   a control system capable of:
      receiving the first biometric data and the second biometric data from the sensor system;
      performing an authentication process based, at least in part, on the first biometric data and the second biometric data, the authentication process being performed without reference to authentication information from an external device; and
      controlling the wearable device according to a result of the authentication process, wherein controlling the wearable device comprises controlling the substance delivery system according to the authentication process.

2. The wearable device of claim 1, wherein controlling the wearable device according to the result of the authentication process involves preventing or ceasing at least one function of the wearable device if the authentication process indicates that the user has not been authenticated.

3. The wearable device of claim 1, further comprising a wireless interface system, wherein the sensor system includes one or more physiological sensors capable of obtaining physiological data from the user's body, and wherein the control system is capable of:
   receiving physiological data from the sensor system; and
   providing, via the wireless interface system, at least some of the physiological data to a second device.

4. The wearable device of claim 3, wherein the physiological data includes at least one type of data selected from the group consisting of temperature data, respiration rate data, oxygen saturation data, blood glucose data, blood pressure data, heart rate data, data indicating electrical activity of the user's heart, actigraphy data and blood alcohol data from the user's body.

5. The wearable device of claim 3, wherein the control system is capable of encrypting the physiological data.

6. The wearable device of claim 3, wherein the control system is capable of decrypting information received from the second device.

7. The wearable device of claim 1, wherein controlling the substance delivery system involves administering a substance to the user.

8. The wearable device of claim 1, wherein the control system includes secure processing and memory resources.

9. The wearable device of claim 1, wherein the first biometric data includes at least one type of data selected from the group consisting of fingerprint data, voice data, retinal data, data indicating electrical activity of the user's heart, hair follicle data, pore data, skin papilla data and sub-dermal blood vessel data.

10. The wearable device of claim 1, wherein the control system is further capable of:
   determining whether the current user is an authorized user by comparing at least one of the first biometric information or the second biometric information with stored biometric information; and
   associating the stored biometric information with at least one of the first biometric information or the second biometric information if the control system determines that the current user is the authorized user.

11. A method of controlling a wearable device, the method comprising:
   obtaining, via a sensor system of the wearable device, first biometric data and second biometric data from a user to whose body the wearable device is currently secured, the first biometric data being a first type of biometric data and the second biometric data being a second type of biometric data;
   performing an authentication process based, at least in part, on the first biometric data and the second biometric data, the authentication process being performed without reference to authentication information from an external device; and controlling the wearable device according to a result of the authentication process, wherein controlling the wearable device comprises controlling a substance delivery system according to the authentication process.

12. The method of claim 11, wherein controlling the wearable device involves administering a substance to the user.

13. The method of claim 11, wherein controlling the wearable device involves preventing or ceasing at least one function of the wearable device if the result of the authentication process indicates that the user has not been authenticated.

14. The method of claim 11, wherein the wearable device includes a wireless interface system and the sensor system includes one or more physiological sensors capable of obtaining physiological data from the user's body, wherein the method further comprises:
receiving physiological data from the sensor system; and
providing, via the wireless interface system, at least some of the physiological data to a second device.

15. The method of claim 14, wherein the physiological data includes at least one type of data selected from the group consisting of temperature data, respiration rate data, oxygen saturation data, blood glucose data, blood pressure data, heart rate data, data indicating electrical activity of the user's heart, actigraphy data and blood alcohol data from the user's body.

16. The method of claim 14, further comprising encrypting the physiological data.

17. The method of claim 14, further comprising decrypting information received from the second device.

18. One or more non-transitory media having instructions stored thereon for performing a method of controlling a wearable device, the method comprising:
obtaining, via a sensor system of the wearable device, first biometric data and second biometric data from a user to whose body the wearable device is currently secured, the first biometric data being a first type of biometric data and the second biometric data being a second type of biometric data;
performing an authentication process based, at least in part, on the first biometric data and the second biometric data, the authentication process being performed without reference to authentication information from an external device; and
controlling the wearable device according to a result of the authentication process, wherein controlling the wearable device comprises controlling a substance delivery system according to the authentication process.

19. The one or more non-transitory media of claim 18, wherein controlling the wearable device involves administering a substance to the user.

20. The one or more non-transitory media of claim 18, wherein controlling the wearable device involves preventing or ceasing at least one function of the wearable device if the result of the authentication process indicates that the user has not been authenticated.

* * * * *